(12) United States Patent
Sue et al.

(10) Patent No.: US 11,475,990 B2
(45) Date of Patent: Oct. 18, 2022

(54) SYSTEMS AND METHODS FOR DELIVERY OF DIGITAL BIOMARKERS AND GENOMIC PANELS

(71) Applicant: PAIGE.AI, Inc., New York, NY (US)

(72) Inventors: Jillian Sue, New York, NY (US); Jason Locke, Westport, CT (US); Peter Schueffler, New York, NY (US); Christopher Kanan, Rochester, NY (US); Thomas Fuchs, New York, NY (US); Leo Grady, Darien, CT (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 17/160,129

(22) Filed: Jan. 27, 2021

(65) Prior Publication Data

US 2021/0233642 A1 Jul. 29, 2021

Related U.S. Application Data

(60) Provisional application No. 62/966,659, filed on Jan. 28, 2020.

(51) Int. Cl.
*G16H 30/20* (2018.01)
*G06N 20/00* (2019.01)

(52) U.S. Cl.
CPC ............ *G16H 30/20* (2018.01); *G06N 20/00* (2019.01)

(58) Field of Classification Search
CPC ............................. G16H 30/20; G06N 20/00
USPC ............................................................. 705/2
See application file for complete search history.

(56) References Cited

U.S. PATENT DOCUMENTS

| | | | |
|---|---|---|---|
| 2016/0364862 A1* | 12/2016 | Reicher | G06K 9/6227 |
| 2018/0018426 A1 | 1/2018 | Hwang et al. | |
| 2018/0232883 A1 | 8/2018 | Sethi et al. | |
| 2020/0211189 A1* | 7/2020 | Yip | G06T 7/11 |
| 2020/0245918 A1* | 8/2020 | Dagum | G06F 3/04886 |
| 2020/0395117 A1* | 12/2020 | Schnorr | G16H 30/40 |
| 2020/0410683 A1* | 12/2020 | Hu | A61B 5/055 |

(Continued)

FOREIGN PATENT DOCUMENTS

WO   WO 2019/172901 A1   9/2019

OTHER PUBLICATIONS

Koelzer, V. H., Sirinukunwattana, K., Rittscher, J., & Mertz, K. D. (2019). Precision immunoprofiling by image analysis and artificial intelligence. Virchows Archiv, 474(4), 511-522. doi:http://dx.doi.org/10.1007/s00428-018-2485-z (Year: 2019).*

*Primary Examiner* — Christopher L Gilligan
*Assistant Examiner* — Bennett Stephen Erickson
(74) *Attorney, Agent, or Firm* — Bookoff McAndrews, PLLC

(57) ABSTRACT

Systems and methods are disclosed for receiving one or more digital images associated with a tissue specimen, a related case, a patient, and/or a plurality of clinical information, determining one or more of a prediction, a recommendation, and/or a plurality of data for the one or more digital images using a machine learning system, the machine learning system having been trained using a plurality of training images, to predict a biomarker and a plurality of genomic panel elements, and determining, based on the prediction, the recommendation, and/or the plurality of data, whether to log an output and at least one visualization region as part of a case history within a clinical reporting system.

19 Claims, 10 Drawing Sheets

(56) References Cited

U.S. PATENT DOCUMENTS

2021/0005308 A1\* 1/2021 Klaiman ............... G06T 7/0012
2021/0166380 A1\* 6/2021 Yip .......................... G06T 1/20

\* cited by examiner

SYSTEMS AND METHODS FOR DELIVERY OF DIGITAL BIOMARKERS AND GENOMIC PANELS

RELATED APPLICATION(S)

This application claims priority to U.S. Provisional Application No. 62/966,659 filed Jan. 28, 2020, the entire disclosure of which is hereby incorporated herein by reference in its entirety.

FIELD OF THE DISCLOSURE

Various embodiments of the present disclosure pertain generally to developing artificial intelligence (AI) technology to detect biomarkers, genomic features, treatment resistance and other relevant features necessary for additional testing of pathology specimens. More specifically, particular embodiments of the present disclosure relate to systems and methods for predicting, identifying or detecting biomarkers and genomic features of prepared tissue specimens. The present disclosure further provides systems and methods for creating a prediction model that predicts labels from unseen slides.

BACKGROUND

There may be multiple steps, incurred costs, and time required for a pathologist to receive results for a Biomarker or Genomics Panel. For a biomarker result, (a) a pathologist may note the appropriate or suspicious part of a patient; (b) a lab may receive the request for a slide stain; (c) the lab cuts the block or finds the appropriate unstained slide; (d) the part is stained; and (e) the test is logged electronically to the case and given to pathologist for final review. For a genomics panel, (a) the request for a molecular test may be given to a pathologist; (b) the pathologist may select a slide from which to sequence; (c) prompt recuts of tissue to be made; (d) prompt a tumor to be scraped based on a pathologist's outline from a previous biopsy cut; (e) genome in the scraped tumor tissue may be sequenced; and (f) a genetic report may be created. These processes can be expensive and time intensive.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for predicting a biomarker and/or at least one genomic feature in a digital image associated with a tissue specimen.

A computer-implemented method for processing an electronic image corresponding to a specimen includes: receiving one or more digital images associated with a tissue specimen, a related case, a patient, and/or a plurality of clinical information; determining one or more of a prediction, a recommendation, and/or a plurality of data for the one or more digital images using a machine learning system, the machine learning system having been trained using a plurality of training images, to predict a biomarker and a plurality of genomic panel elements; and determining, based on the prediction, the recommendation, and/or the plurality of data, whether to log an output and at least one visualization region as part of a case history within a clinical reporting system.

A system for processing an electronic image corresponding to a specimen includes a memory storing instructions; and at least one processor executing the instructions to perform a process including receiving one or more digital images associated with a tissue specimen, a related case, a patient, and/or a plurality of clinical information; determining one or more of a prediction, a recommendation, and/or a plurality of data for the one or more digital images using a machine learning system, the machine learning system having been trained using a plurality of training images, to predict a biomarker and a plurality of genomic panel elements; and determining, based on the prediction, the recommendation, and/or the plurality of data, whether to log an output and at least one visualization region as part of a case history within a clinical reporting system.

A non-transitory computer-readable medium storing instructions that, when executed by a processor, cause the processor to perform a method for processing an electronic image corresponding to a specimen includes: receiving one or more digital images associated with a tissue specimen, a related case, a patient, and/or a plurality of clinical information, determining one or more of a prediction, a recommendation, and/or a plurality of data for the one or more digital images using a machine learning system, the machine learning system having been trained using a plurality of training images, to predict a biomarker and a plurality of genomic panel elements, and determining, based on the prediction, the recommendation, and/or the plurality of data, whether to log an output and at least one visualization region as part of a case history within a clinical reporting system.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
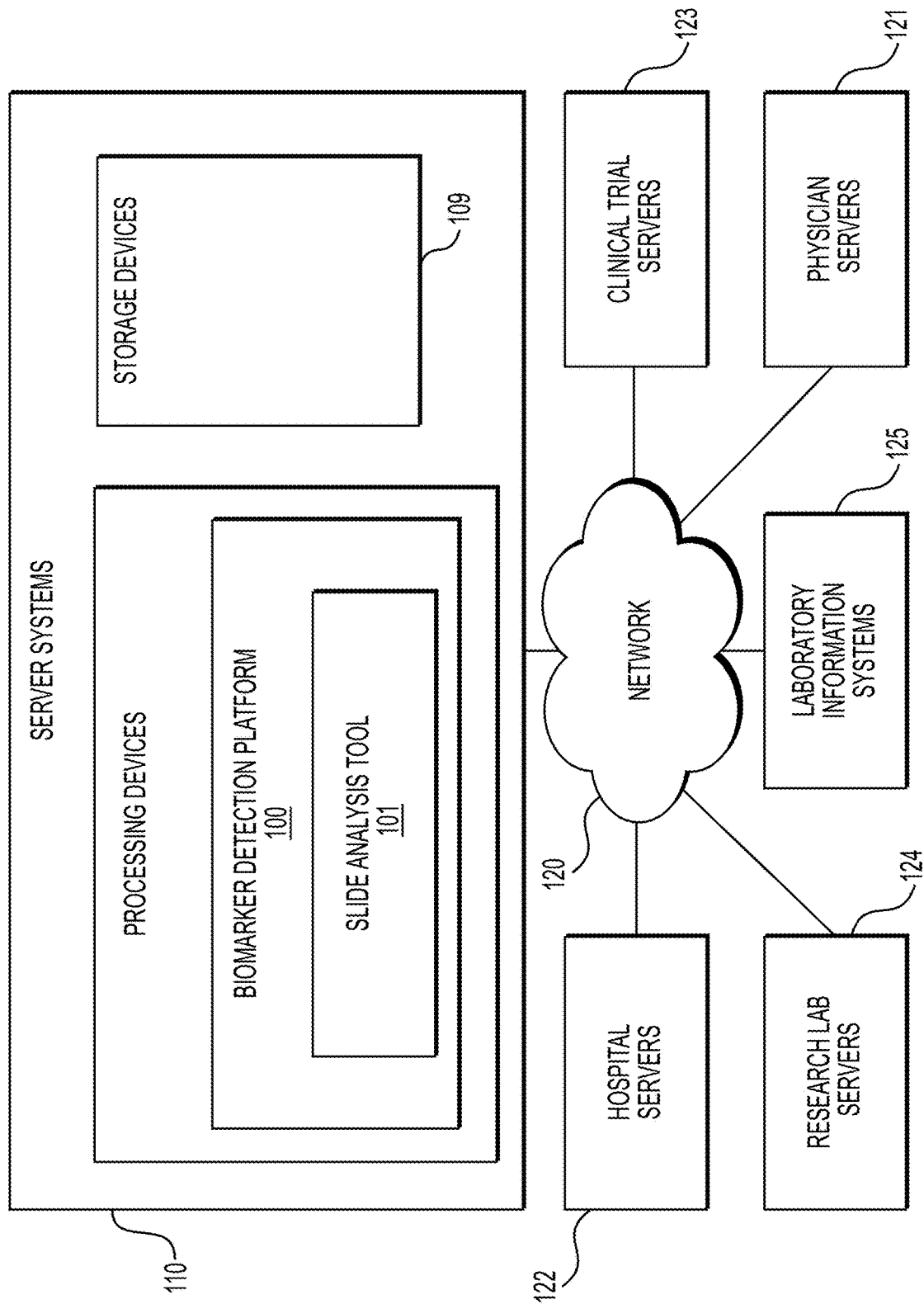
FIG. 1A illustrates an exemplary block diagram of a system and network for detecting a biomarker and/or at least one genomic feature, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that these steps must be performed in the order presented but may instead by performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Pathology refers to the study of diseases, as well as the causes and effects of disease. More specifically, pathology refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis. When uncertain of a diagnostic finding on a slide, a pathologist may order additional cut levels, stains, or other tests to gather more information from the tissue. Technician(s) may then create new slide(s) which may contain the additional information for the pathologist to use in making a diagnosis. This process of creating additional slides may be time-consuming, not only because it may involve retrieving the block of tissue, cutting it to make a new a slide, and then staining the slide, but also because it may be batched for multiple orders. This may significantly delay the final diagnosis that the pathologist renders. In addition, even after the delay, there may still be no assurance that the new slide(s) will have information sufficient to render a diagnosis.

Pathologists may evaluate cancer and other disease pathology slides in isolation. The present disclosure presents a method of using AI to detect and predict biomarkers and genomic panel features. In particular, the present disclosure describes various exemplary user interfaces available in the workflow, as well as AI tools that may be integrated into the workflow to expedite and improve a pathologist's work.

For example, computers may be used to analyze an image of a tissue sample to quickly identify whether additional information may be needed about a particular tissue sample, and/or to highlight to a pathologist an area in which he or she should look more closely. Thus, the process of obtaining additional stained slides and tests may be done automatically before being reviewed by a pathologist. When paired with automatic slide segmenting and staining machines, this may provide a fully automated slide preparation pipeline. This automation has, at least, the benefits of (1) minimizing an amount of time wasted by a pathologist determining a slide to be insufficient to make a diagnosis, (2) minimizing the (average total) time from specimen acquisition to diagnosis by avoiding the additional time between when additional tests are ordered and when they are produced, (3) reducing the amount of time per recut and the amount of material wasted by allowing recuts to be done while tissue blocks (e.g., pathology specimens) are in a cutting desk, (4) reducing the amount of tissue material wasted/discarded during slide preparation, (5) reducing the cost of slide preparation by partially or fully automating the procedure, (6) allowing automatic customized cutting and staining of slides that would result in more representative/informative slides from samples, (7) allowing higher volumes of slides to be generated per tissue block, contributing to more informed/ precise diagnoses by reducing the overhead of requesting additional testing for a pathologist, and/or (8) identifying or verifying correct properties (e.g., pertaining to a specimen type) of a digital pathology image, etc.

The process of using computers to assist pathologists is known as computational pathology. Computing methods used for computational pathology may include, but are not limited to, statistical analysis, autonomous or machine learning, and AI. AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting slides suspicious for cancer, thereby allowing pathologists to check and confirm their initial assessments before rendering a final diagnosis.

As described above, computational pathology processes, and devices of the present disclosure, may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

The present disclosure is directed to systems and methods for quickly and correctly identifying and/or verifying a specimen type of a digital pathology image, or any information related to a digital pathology image, without necessarily accessing an LIS or analogous information database. One embodiment of the present disclosure may include a system trained to identify various properties of a digital pathology image, based on datasets of prior digital pathology images. The trained system may provide a classification for a specimen shown in a digital pathology image. The classification may help to provide treatment or diagnosis prediction(s) for a patient associated with the specimen.

The systems and methods of the present disclosure may use artificial intelligence to detect a scanned slide with any feature that may be a predicate to further testing (e.g., the highest tumor volume for molecular or invasive for human epidermal growth factor receptor 2/estrogen receptor/progesterone receptor (HER2/ER/PR)). This feature detection may be accomplished at the case, part, or block levels of a specimen. The results may be available via any user interface (e.g., through a viewer, report, through a laboratory information system (LIS), etc.). The systems and methods of the present disclosure may also provide immediate visualization of a predicted immunohistochemistry (IHC) result, genomics panel, derived information using AI (e.g., treatment resistance), etc., from one or digital pathology specimen images acquired from a patient. This may provide turnaround time and cost efficiencies for both the hospitals and patients. In addition to showing the results of a digital IHC or digital genomic panel, the present system may further manage the reimbursement elements for that purchase. This may provide additional efficiency for hospitals and patients.

The systems and methods of the present disclosure may use artificial intelligence to detect a scanned slide with any feature that may be a predicate to further testing (e.g., the highest tumor volume for molecular or invasive for human epidermal growth factor receptor 2/estrogen receptor/progesterone receptor (HER2/ER/PR)). This feature detection may be accomplished at the case, part, or block levels of a specimen. The results may be available via any user interface (e.g., through a viewer, report, through a laboratory information system (LIS), etc.). The systems and methods of the present disclosure may also provide immediate visualization of a predicted immunohistochemistry (IHC) result, genomics panel, derived information using AI (e.g., treatment resistance), etc., from one or digital pathology specimen images acquired from a patient. This may provide turnaround time and cost efficiencies for both the hospitals and the patients. In addition to showing the results of a digital IHC or digital genomic panel, the present system may further manage the reimbursement elements for that order. This may provide additional efficiency for hospitals and patients.

This disclosure includes one or more embodiments of a slide analysis tool. The input to the tool may include a digital pathology image and any relevant additional inputs. Outputs of the tool may include global and/or local information about the specimen. A specimen may include a biopsy or surgical resection specimen.

Exemplary global outputs of the disclosed tool(s) may contain information about an entire image, e.g., the specimen type, the overall quality of the cut of the specimen, the overall quality of the glass pathology slide itself, and/or tissue morphology characteristics. Exemplary local outputs may indicate information in specific regions of an image, e.g., a particular image region may be classified as having blur or a crack in the slide. The present disclosure includes embodiments for both developing and using the disclosed slide analysis tool(s), as described in further detail below.

FIG. 1A illustrates a block diagram of a system and network for determining specimen property or image property information pertaining to digital pathology images, using machine learning, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present disclosure, the electronic network 120 may also be connected to server systems 110, which may include processing devices that are configured to implement a biomarker detection platform 100, which includes a slide analysis tool for determining specimen property or image property information pertaining to digital pathology images, and using machine learning to create a genomic panel, according to an exemplary embodiment of the present disclosure.

The physician servers 121, hospital servers 122, clinical trial servers 123, research lab servers 124, and/or laboratory information systems 125 may create or otherwise obtain images of one or more patient's cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the one or more storage devices 109. Server systems 110 may further include one or more machine learning tool(s) or capabilities. For example, the processing devices may include a machine learning tool for a biomarker detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in a laboratory information system 125. However, the correct tissue classification information is not always paired with the image content. Additionally, even if an LIS is used to access the specimen type for a digital pathology image, this label may be incorrect due to the fact that many components of an LIS may be manually inputted, leaving a large margin for error. According to an exemplary embodiment of the present disclosure, a specimen type may be identified without needing to access the library information systems 125, or may be identified to possibly correct library information systems 125. For example, a third party may be given anonymized access to the image content without the corresponding specimen type label stored in the LIS. Additionally, access to LIS content may be limited due to its sensitive content.

Figure 1B:
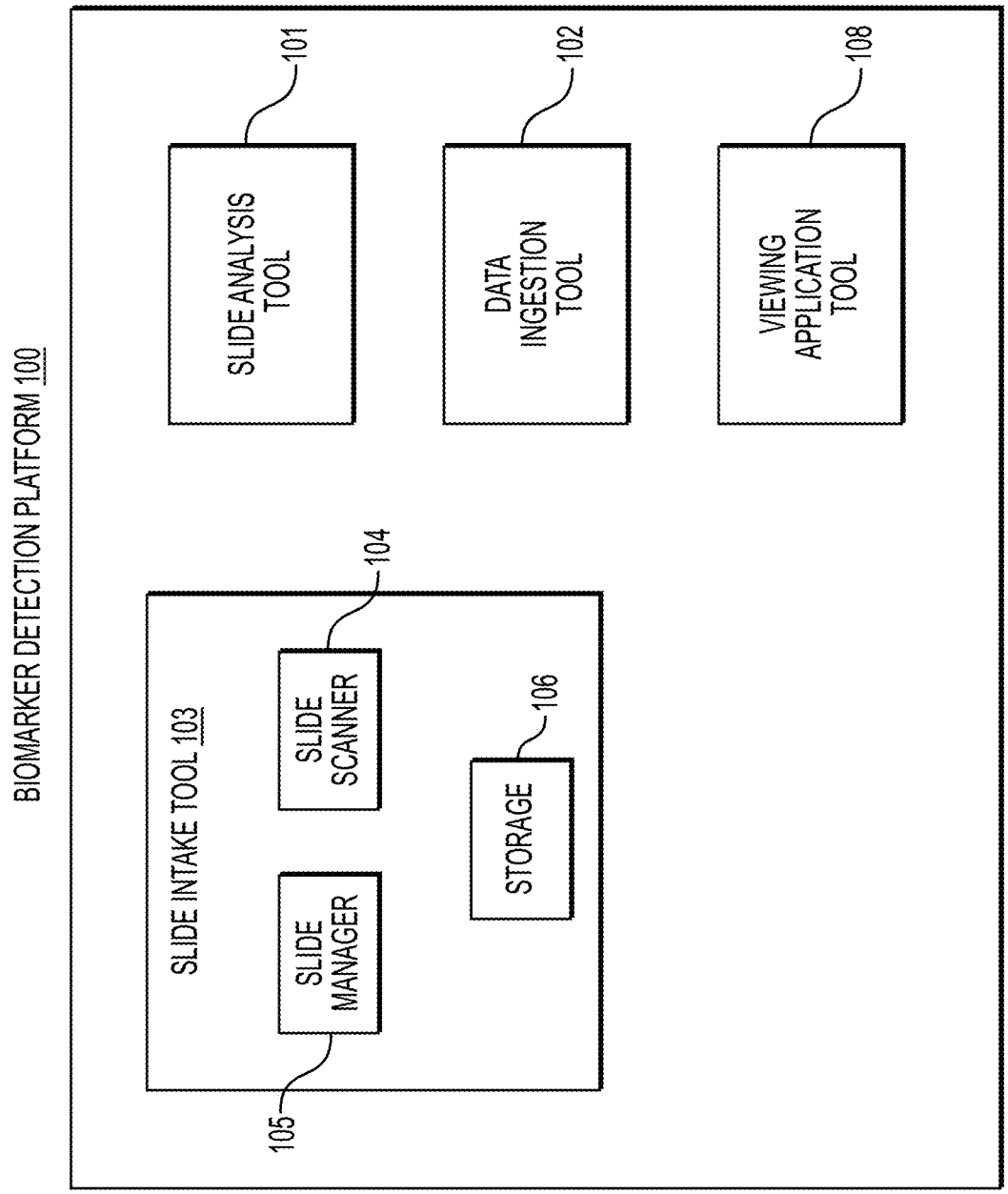
FIG. 1B illustrates an exemplary block diagram of a biomarker detection platform for predicting biomarkers and genomic panel features, using machine learning, according to an embodiment of the present disclosure.

FIG. 1B illustrates an exemplary block diagram of a biomarker detection platform for predicting biomarkers and genomic panel features, using machine learning, according to an embodiment of the present disclosure.

Specifically, FIG. 1B depicts components of the biomarker detection platform 100, according to one embodiment. For example, the biomarker detection platform 100 may include a slide analysis tool 101, a data ingestion tool 102, a slide intake tool 103, a slide scanner 104, a slide manager 105, a storage 106, and a viewing application tool 108.

The slide analysis tool 101, as described below, refers to a process and system for processing digital images associated with a tissue specimen, and using machine learning to analyze a slide, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., a pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and each of its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include one or more storage devices 109 for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the one or more storage devices 109. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools and modules may be located on a device that may be connected to an electronic network 120, such as the Internet or a cloud service provider, through one or more computers, servers, and/or handheld mobile devices.

Figure 1C:
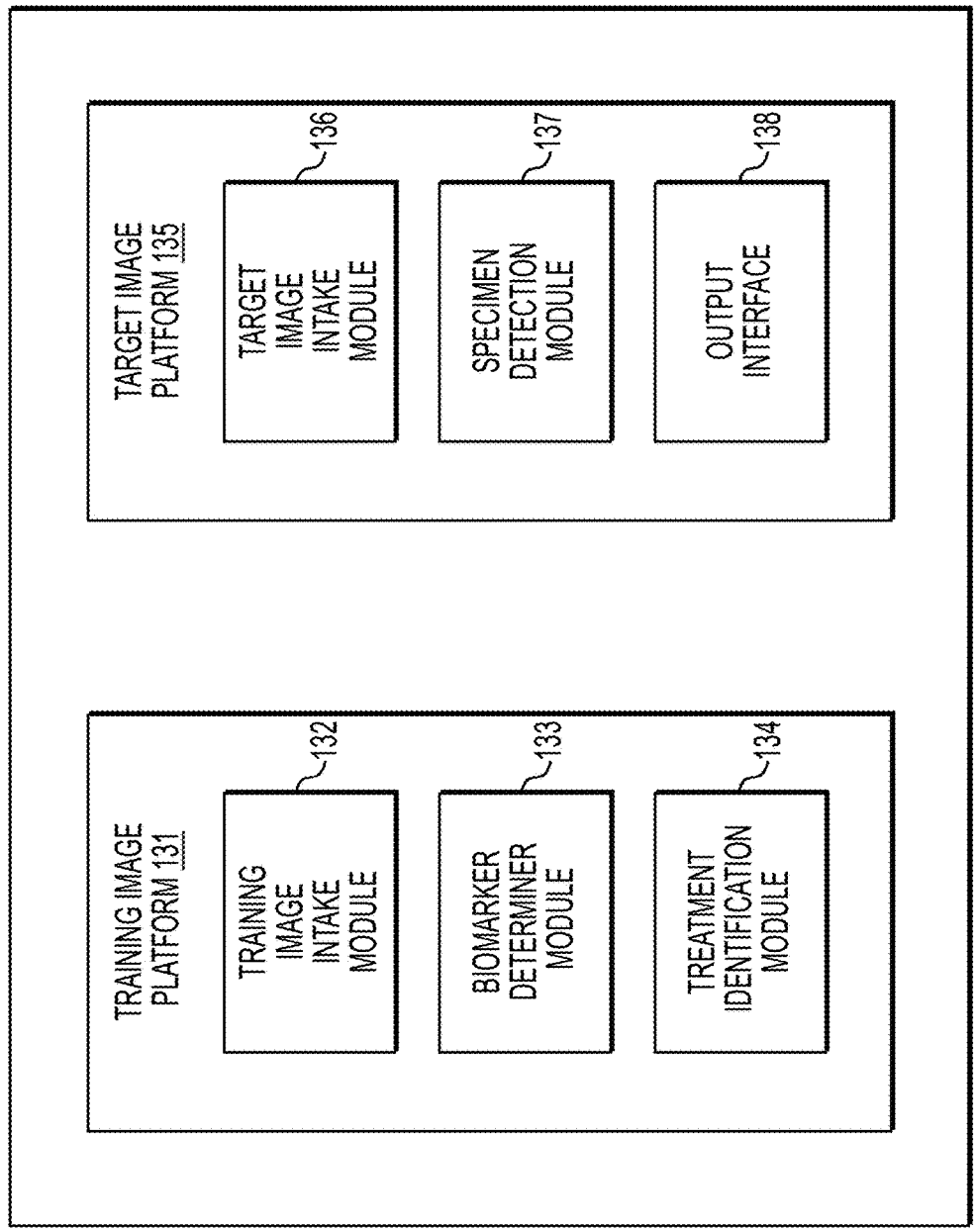
FIG. 1C illustrates an exemplary block diagram of a slide analysis tool, according to an exemplary embodiment of the present disclosure.

FIG. 1C illustrates an exemplary block diagram of a slide analysis tool 101, according to an exemplary embodiment of the present disclosure. The slide analysis tool 101 may include a training image platform 131 and/or a target image platform 135.

The training image platform 131, according to one embodiment, may create or receive training images that are used to train a machine learning system to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hemotoxylin alone, IHC, molecular pathology, etc.; and/or (b) digitized tissue samples from a 3D imaging device, such as microCT.

The training image intake module 132 may create or receive a dataset comprising one or more training images corresponding to either or both of images of a human tissue and images that are graphically rendered. For example, the training images may be received from any one or any combination of the server systems 110, physician servers 121, hospital servers 122, clinical trial servers 123, research lab servers 124, and/or laboratory information systems 125. This dataset may be kept on a digital storage device. The quality score determiner module 133 may identify quality control (QC) issues (e.g., imperfections) for the training images at a global or local level that may greatly affect the usability of a digital pathology image. For example, the quality score determiner module may use information about an entire image, e.g., the specimen type, the overall quality of the cut of the specimen, the overall quality of the glass pathology slide itself, or tissue morphology characteristics, and determine an overall quality score for the image. The treatment identification module 134 may analyze images of tissues and determine which digital pathology images have treatment effects (e.g., post-treatment) and which images do not have treatment effects (e.g., pre-treatment). It is useful to identify whether a digital pathology image has treatment effects because prior treatment effects in tissue may affect the morphology of the tissue itself. Most LIS do not explicitly keep track of this characteristic, and thus classifying specimen types with prior treatment effects can be desired.

According to one embodiment, the target image platform 135 may include a target image intake module 136, a specimen detection module 137, and an output interface 138. The target image platform 135 may receive a target image and apply the machine learning model to the received target image to determine a characteristic of a target specimen. For example, the target image may be received from any one or any combination of the server systems 110, physician servers 121, hospital servers 122, clinical trial servers 123, research lab servers 124, and/or laboratory information systems 125. The target image intake module 136 may receive a target image corresponding to a target specimen. The specimen detection module 137 may apply the machine learning model to the target image to determine a characteristic of the target specimen. For example, the specimen detection module 137 may detect a specimen type of the target specimen. The specimen detection module 137 may also apply the machine learning model to the target image to determine a quality score for the target image. Further, the specimen detection module 137 may apply the machine learning model to the target specimen to determine whether the target specimen is pretreatment or post-treatment.

The output interface 138 may be used to output information about the target image and the target specimen (e.g., to a screen, monitor, storage device, web browser, etc.).

Figure 2A:
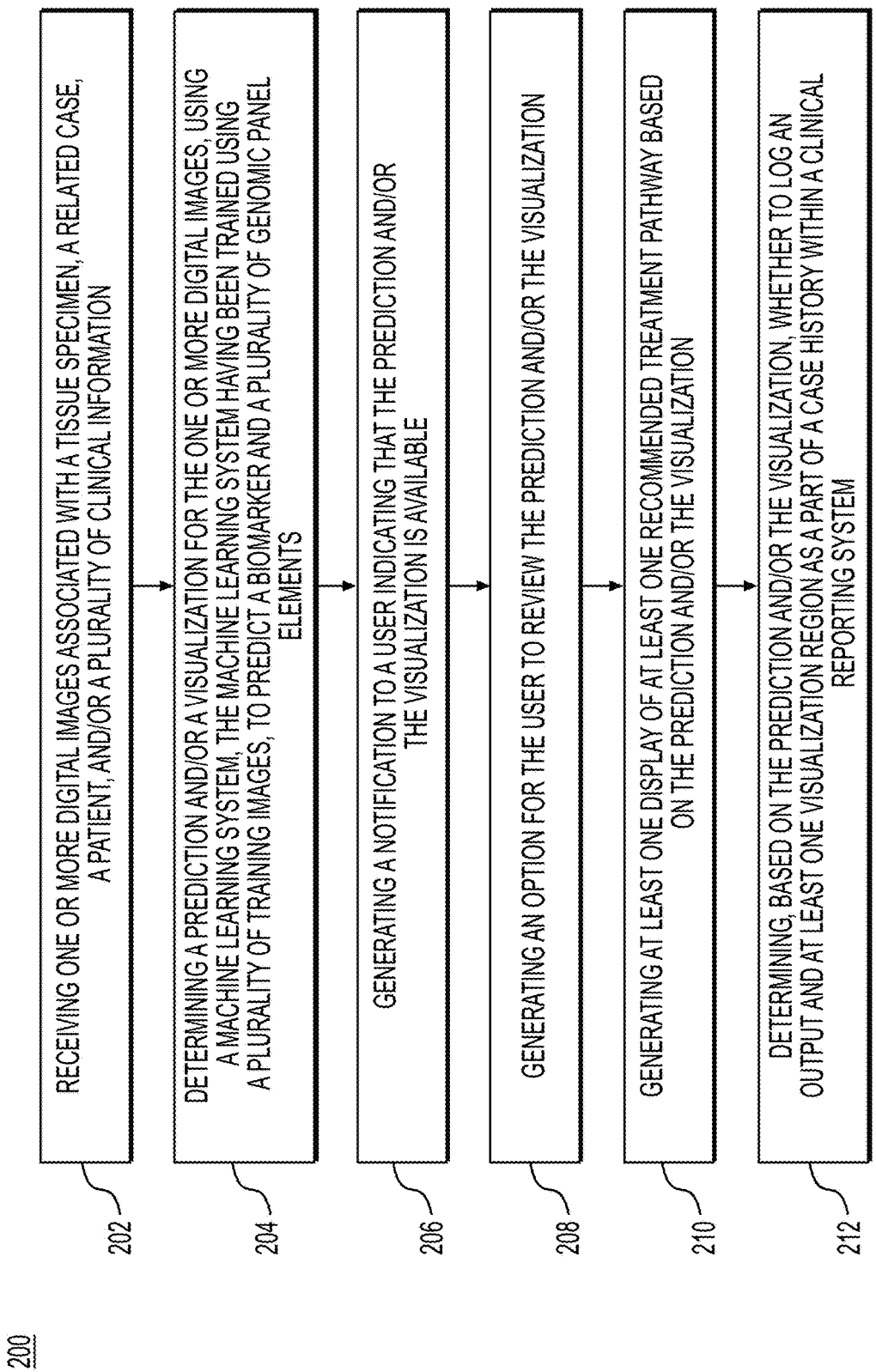
FIG. 2A is a flowchart illustrating an exemplary method for using a machine learning system to detect a biomarker and/or at least one genomic feature, according to one or more exemplary embodiments of the present disclosure.

FIG. 2A is a flowchart illustrating an exemplary method for using a machine learning system to predict a biomarker and at least one genomic panel element, according to one or more exemplary embodiments of the present disclosure. For example, an exemplary method 200 (i.e., steps 202-212) may be performed by slide analysis tool 101 automatically or in response to a request from a user.

According to one embodiment, the exemplary method 200 for predicting a biomarker and at least one genomic panel element may include one or more of the following steps. In step 202, the method may include receiving one or more digital images associated with a tissue specimen, a related case, a patient, and/or a plurality of clinical information. The tissue specimen may comprise a histology specimen, whereas the patient information may include a specimen type, a case and patient ID, a part within a case, a gross description, etc. The plurality of clinical information may include an assigned pathologist, whether a related specimen is available for tests, etc. The digital images may be received into a digital storage device (e.g., a hard drive, a network drive, a cloud storage, a random access memory (RAM), etc.).

In step 204, the method may include determining a predication and/or a visualization for the one or more digital images, using a machine learning system, the machine learning system having been trained using a plurality of training images, to predict a biomarker and at least one genomic panel element. The machine learning system may additionally output a recommendation and/or data to an electronic storage device.

In step 206, the method may include generating a notification to a user indicating that the prediction and/or the visualization is available. The notification may comprise a visual display, a pop-up window, or other suitable alert.

Figure 6:
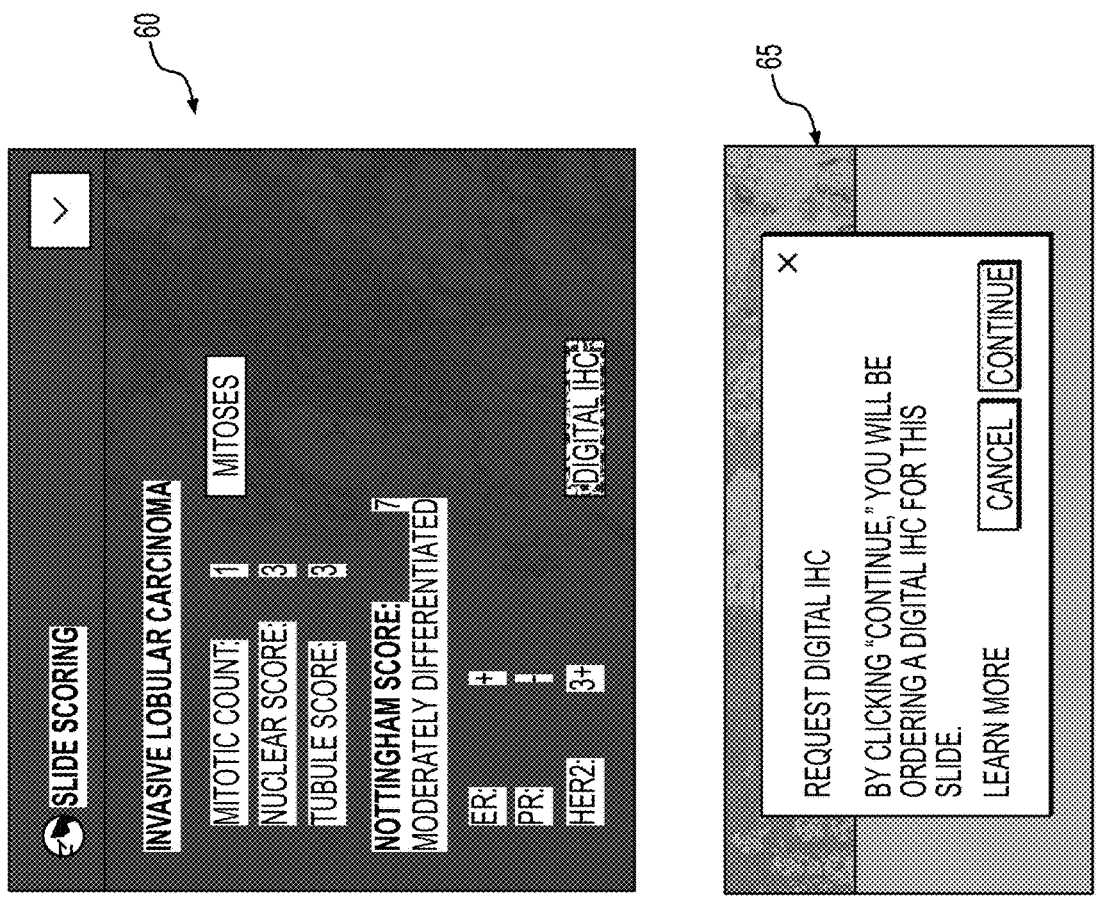
FIG. 6 depicts exemplary options for a user to review a visualization and/or report, according to one or more exemplary embodiments of the present disclosure.

In step 208, the method may include generating an option for the user to review the prediction and/or the visualization. The option may include an exemplary screen display as illustrated in FIG. 6, discussed below.

In step 210, the method may include generating at least one display of at least one recommended treatment pathway based on the prediction and/or the visualization. The at least one recommended treatment pathway may include a validated treatment pathway, a new treatment pathway, a clinical treatment pathway, etc., or next steps (e.g., clinical trials, a specialized doctor visit, etc.), based on the generated prediction. A visualization of a digital immunohistochemistry or a genomic panel result may be accomplished using a number of methods, including but not limited to:
  a. Overlaying at least one region of interest on top of an original image;
  b. Side by side visualization;
  c. Reporting with quantification measures; and
  d. Summarizing digital tests run with results.

The visualization of the recommendation may comprise an interactive web interface, where a user (e.g., pathologist, oncologist, patient, etc.) may learn more about a specific recommendation (e.g., open clinical trials, hospital/physicians that specialize in a treatment, etc.) via the interface's direct links and sources (e.g., websites, literature, etc.). Alternatively, the visualization may comprise a report, wherein the user may view a summarized, immutable report that may include, but is not limited to the following elements:
  a. Patient history
  b. Case summary
  c. Diagnostic summary
  d. Digital and/or 'manual' test results
  e. Suggested next steps for patient based on digital test results The method may group together similar patients (e.g., patients with similar morphological patterns, similar biomarker expression, similar genomic profile, similar treatment pathways, or other similarities) as reference to a given case, to support the decision-making process for a particular case. A visualization of similar patients may or may not be in context to recommended treatment pathways for a case. A user (e.g., a pathologist, an oncologist, a patient, etc.) may learn more about specific patients and their outcomes (e.g., from clinical trials, drugs, etc.). The results may be visualized by the interactive web interface (e.g., ways to filter, share, save, etc.), or by report, as disclosed above.

The results may be in the form of a consolidated report comprising report predictions and related information (e.g., a PDF). An exemplary report may contain one or more of the following elements:
  a. Patient history
  b. Patient summary
  c. Case summary
  d. Digital tests completed
  e. Digital test results
  f. Synthesized summary of results and what results may mean for the patient
  g. Visualization of statistics (e.g., infographic, interactive website, etc.) for outcome based on similar patients
  h. Summary of relevant and/or recent literature
  i. Suggested next steps (e.g., clinical trials, drugs, chemotherapy, etc.), etc.

In step 212, the method may include determining, based on the prediction and/or the visualization, whether to log an output and at least one visualization region as a part of a case history within a clinical reporting system. The method may also include integrating the recommendations and the visualizations into a final diagnostic report for the specimen.

Figure 2B:
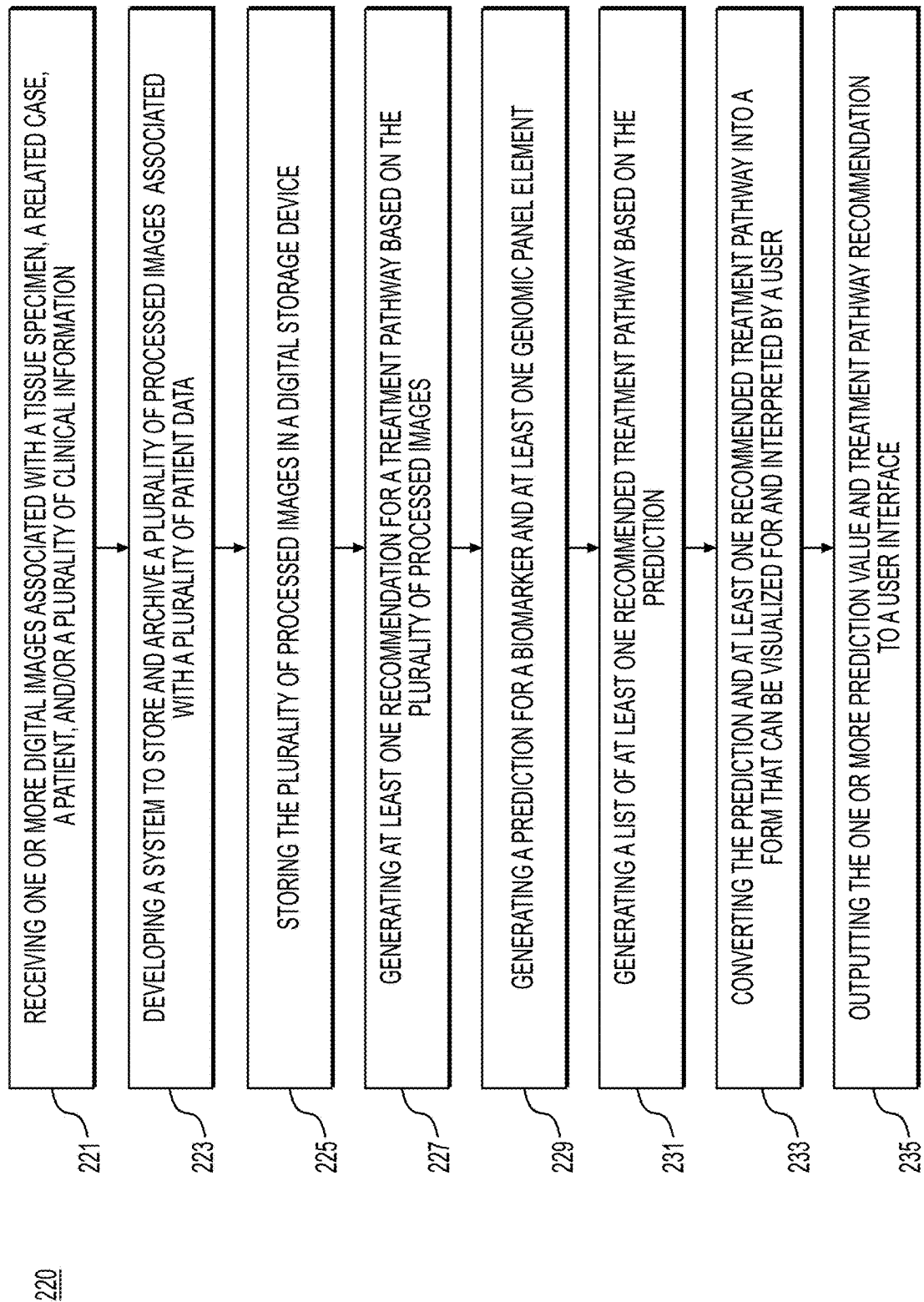
FIG. 2B is a flowchart illustrating an exemplary method for training a machine learning system to detect a biomarker and/or at least one genomic feature according to one or more exemplary embodiments of the present disclosure.

FIG. 2B is a flowchart illustrating an exemplary method for training a machine learning system to predict a biomarker and at least one genomic panel element, according to one or more exemplary embodiments of the present disclosure. For example, an exemplary method 220 (i.e., steps 221-235) may be performed by slide analysis tool 101 automatically or in response to a request from a user.

According to one embodiment, the exemplary method 220 for training a machine learning system to predict a biomarker and at least one genomic panel element. In step 221, the method may include receiving one or more digital images associated with a tissue specimen, a related case, a patient, and/or a plurality of clinical information. The tissue specimen may comprise a histology specimen, whereas the patient information may include a specimen type, a case and patient ID, a part within a case, a gross description, etc. The plurality of clinical information may include an assigned pathologist, whether a related specimen is available for tests, etc. The digital images may be received into a digital storage device (e.g., a hard drive, a network drive, a cloud storage, a random access memory (RAM), etc.).

In step 223, the method may include developing a system to store and archive a plurality of processed images associated with a plurality of patient data.

In step 225, the method may include storing the plurality of processed images in a digital storage device. The digital storage device may comprise a hard drive, a network drive, a cloud storage, a RAM, etc.

In step 227, the method may include generating at least one recommendation for a treatment pathway based on the plurality of processed images. The treatment pathway may comprise a clinical trial, a treatment, etc. The recommendation may be for a patient, and may be based on at least one relevant feature of a plurality of stored images and patient data (e.g., patient diagnosis, history, demographics, etc.). The recommendations of treatment pathways may comprise or be based on clinical practice guidelines, which may be customized based on patient demographics, pre-approval-stage medicines or therapies, clinical practice, etc.

In step 229, the method may include generating a prediction for a biomarker and at least one genomic panel element.

In step 231, the method may include generating a list of at least one recommended treatment pathway based on the prediction. The list of the at least one recommended treatment pathway may comprise a drug treatment, a clinical trial, etc., and related information (e.g., success rate, locations for treatment, etc.) based on predicted biomarker and genomic panel elements.

In step 233, the method may include converting the prediction and at least one recommended treatment pathway into a form that can be visualized for and interpreted by a user (e.g., pathologist, patient, oncologist, etc.). The method may additionally include outputting or displaying at least one result in various effective formats depending on the user and the use case (e.g., interactive, structured, templatized, static, etc.).

In step 235, the method may include outputting the one or more prediction value and treatment pathway recommendation to a user interface. Outputting or displaying the results may be in various effective formats depending on a user and use case (e.g., interactive, structured, templatized, static, etc.).

Figure 3:
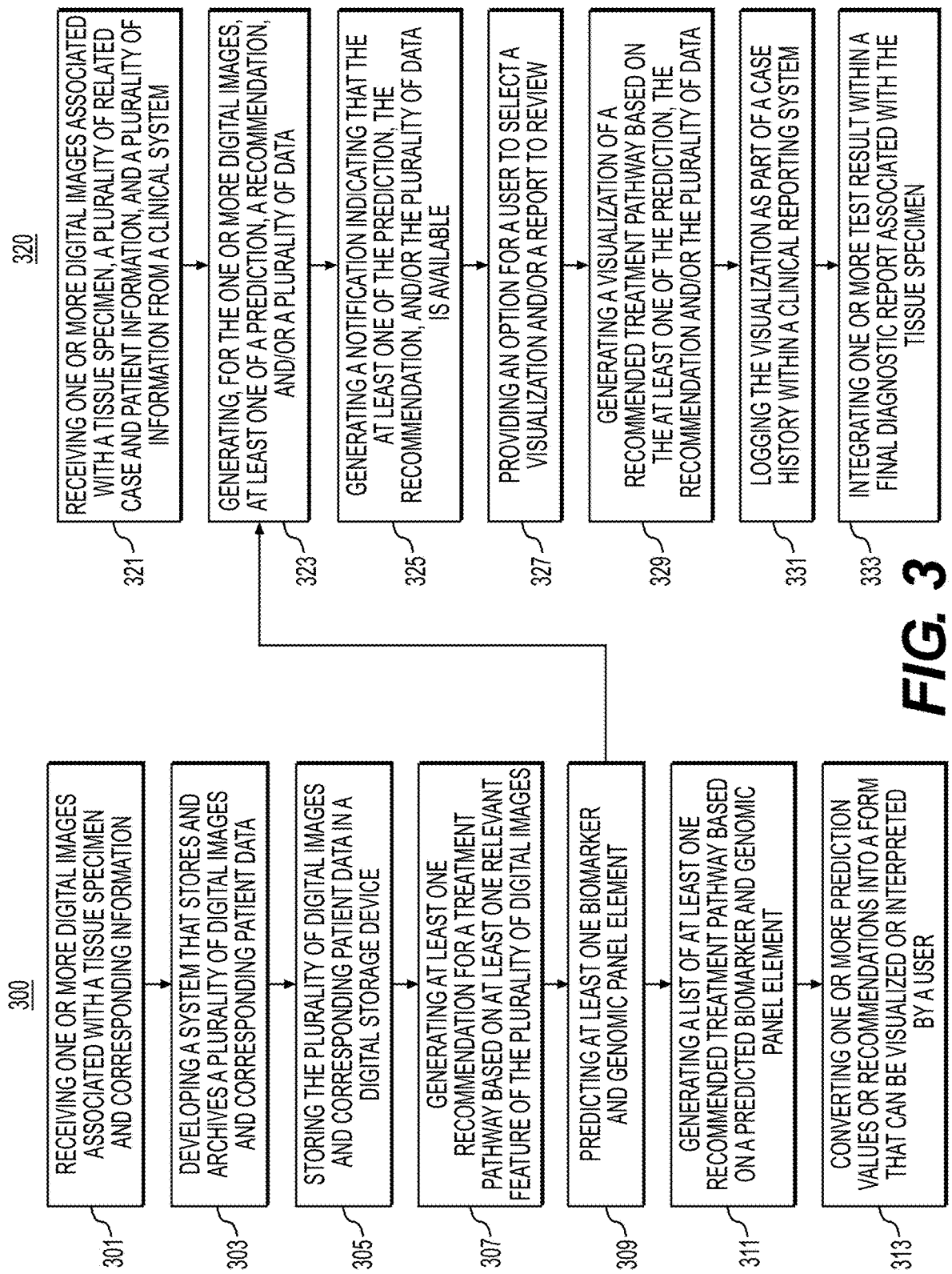
FIG. 3 is a flowchart illustrating an exemplary method for visualizing a positive biomarker foci, according to one or more exemplary embodiments of the present disclosure.

FIG. 3 is a flowchart illustrating an exemplary method for using and training a machine learning system to visualize positive biomarker foci, according to one or more exemplary embodiments of the present disclosure. Visualization of biomarkers (e.g., IHC markers, genomic panels) may aide a pathologist in understanding how a computational assay is behaving. The exemplary methods 300 and 320 may be used to visually display detected positive biomarker foci. Exemplary methods 300 and 320 (i.e., steps 301-313 and steps 321-333) may be performed by slide analysis tool 101 automatically or in response to a request from a user.

According to one embodiment, the exemplary method 300 for training a machine learning system to visualize a positive biomarker foci may include one or more of the following steps. In step 301, the method may include receiving one or more digital images associated with a tissue specimen and corresponding information. The one or more digital images may comprise histology slides. The corresponding information may comprise related information (e.g., specimen type, available parts, gross description, etc.), clinical information (e.g., diagnosis, biomarker information, etc.), and patient information (e.g., demographics, gender, etc.).

In step 303, the method may include developing a system that stores and archives a plurality of digital images and corresponding patient data. The corresponding patient data may comprise images from screening, follow-up, outcome, etc.

In step 305, the method may include storing the plurality of digital images and corresponding patient data in a digital storage device. The digital storage device may comprise a hard drive, a network drive, a cloud storage, a RAM, etc.

In step 307, the method may include generating at least one recommendation for a treatment pathway based on at least one relevant feature of the plurality of digital images. The treatment pathway may include clinical trials, treatments, etc., for a patient based on at least one relevant factors (e.g., patient diagnosis, history, demographics, etc.).

In step 309, the method may include predicting at least one biomarker and genomic panel element.

In step 311, the method may include generating a list of at least one recommended treatment pathway based on a predicted biomarker and genomic panel element. The recommended treatment pathway (e.g., drugs, clinical trials, etc.) and any related information (e.g., success rates, locations for treatment, etc.) may be based on the predicted biomarker and genomic panel elements.

In step 313, the method may include converting one or more prediction values or recommendations into a form that can be visualized or interpreted by a user (e.g., pathologist, patient, oncologist, etc.).

In step 321, the method may include receiving one or more digital images associated with a tissue specimen, a plurality of related case and patient information from a clinical system. The pathology specimen (e.g., histology specimen), the related case and patient information (e.g., specimen type, case and patient ID, parts within case, gross description, etc.) and information from the clinical system (e.g., assigned pathologist, specimens available for tests, etc.) into a digital storage device (e.g., hard drive, network drive, cloud storage, RAM, etc.)

In step 323, the method may include generating, for the one or more digital images, at least one of a prediction, a recommendation, and/or a plurality of data.

In step 325, the method may include generating a notification indicating that the at least one of the prediction, the recommendation, and/or the plurality of data is available. Additionally, a visualization for either an immunohistochemistry or genomic panel may be available.

In step 327, the method may include providing an option for a user to select a visualization and/or a report to review. The user may be a pathologist.

In step 329, the method may include generating a visualization of a recommended treatment pathway based on the at least one of the prediction, the recommendation, and/or the plurality of data. The treatment pathway (e.g., validated, new, clinical, etc.) or next steps (e.g., clinical trials, specialized doctor visit, etc.) may be based on the output/generated predictions. Visualizations of digital immunohistochemistry or genomic panel results can include one or more of a/an:

a. Overlaying (e.g., outline, gradient with color mapping to algorithmic predictions, etc.) on positive regions of interests on the original image b. Side-by-side comparisons of an image with digital IHC or genomics panel prediction display and an image without prediction display c. Prioritized list (e.g., slideshow of image crops, interface that allows the user to jump from one focus to another, etc.) of all positive focal points identified as positive areas for the biomarker or mutation of interest d. Report that either summarizes all tests into one final output (e.g., score, result, recommendation, etc.) or lists a final output for each digital test.

In step 331, the method may include logging the visualization as a part of a case history within a clinical reporting system.

In step 333, the method may include integrating one or more test result within a final diagnostic report associated with the tissue specimen.

Figure 4:
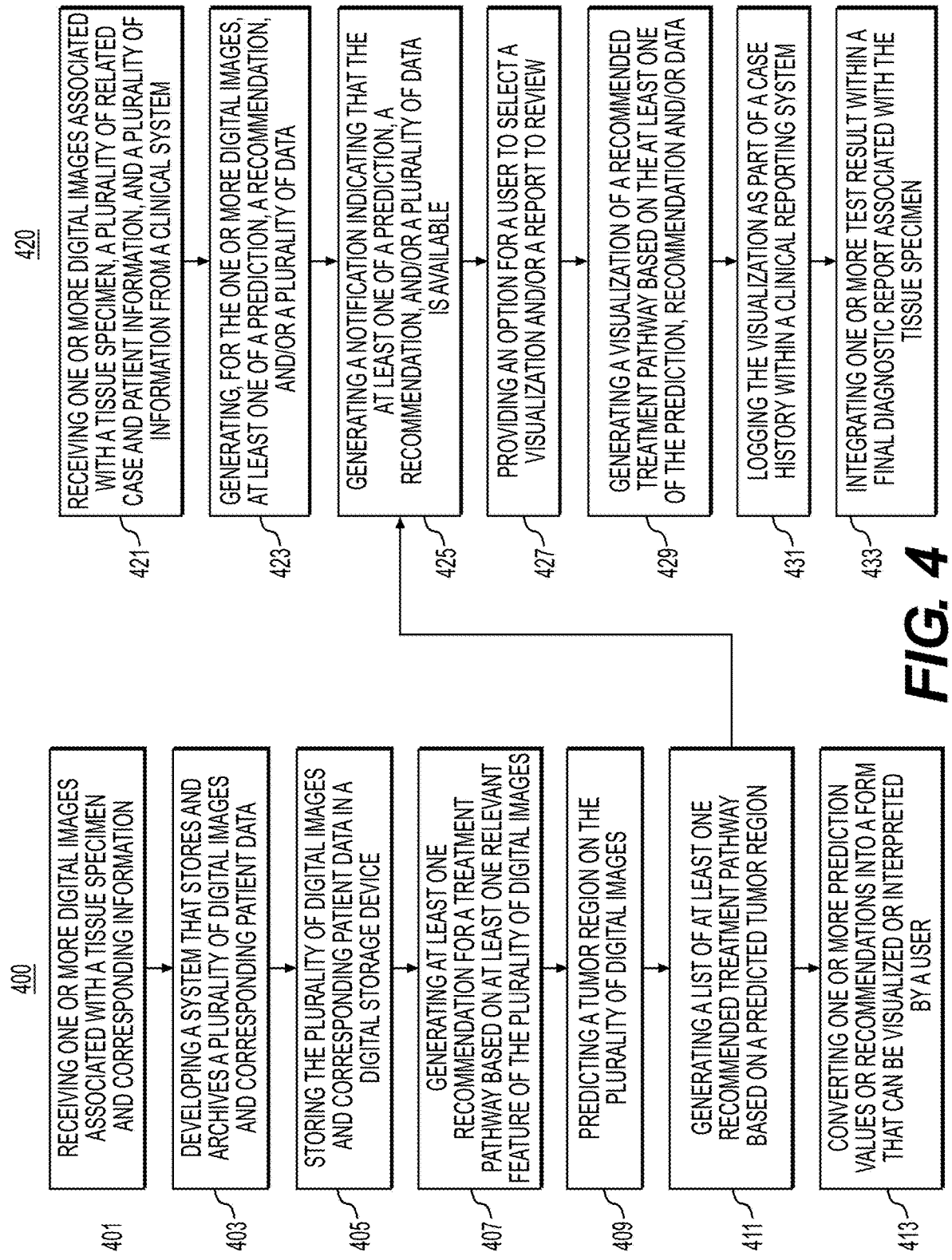
FIG. 4 is a flowchart illustrating an exemplary method for visualizing a tumor region to guide a molecular pathologist, according to one or more exemplary embodiments of the present disclosure.

FIG. 4 is a flowchart illustrating an exemplary method for using and training a machine learning system to visualize tumor region to guide a molecular pathologist, according to one or more exemplary embodiments of the present disclosure. Visualization of a region of malignant tissue on a digitized pathology slide can aide a molecular pathologist in assessing optimal downstream testing. An exemplary embodiment may be used to select an optimal region for downstream testing. The exemplary methods 400 and 420 may be used to visualize tumor region to guide a molecular pathologist. Exemplary methods 400 and 420 (i.e., steps 401-413 and steps 421-433) may be performed by slide analysis tool 101 automatically or in response to a request from a user.

According to one embodiment, the exemplary method 400 for training a machine learning system to visualize tumor region to guide a molecular pathologist may include one or more of the following steps. In step 401, the method may include receiving one or more digital images associated with a tissue specimen and corresponding information. The one or more digital images may comprise histology slides. The corresponding information may comprise related information (e.g., specimen type, available parts, gross description, etc.), clinical information (e.g., diagnosis, biomarker information, etc.), and patient information (e.g., demographics, gender, etc.).

In step 403, the method may include developing a system that stores and archives a plurality of digital images and corresponding patient data. The corresponding patient data may comprise images from screening, follow-up, outcome, etc.

In step 405, the method may include storing the plurality of digital images and corresponding patient data in a digital storage device. The digital storage device may comprise a hard drive, a network drive, a cloud storage, a RAM, etc.

In step 407, the method may include generating at least one recommendation for a treatment pathway based on at least one relevant feature of the plurality of digital images. The treatment pathway may include clinical trials, treatments, etc., for a patient based on at least one relevant factors (e.g., patient diagnosis, history, demographics, etc.).

In step 409, the method may include predicting a tumor region on the plurality of digital images.

In step 411, the method may include generating a list of at least one recommended treatment pathway based on a predicted tumor region. The recommended treatment pathway (e.g., drugs, clinical trials, etc.) and any related information (e.g., success rates, locations for treatment, etc.) may be based on the predicted tumor region.

In step 413, the method may include converting one or more prediction values or recommendations into a form that can be visualized or interpreted by a user (e.g., pathologist, patient, oncologist, etc.).

In step 421, the method may include receiving one or more digital images associated with a tissue specimen, a plurality of related case and patient information from a clinical system. The pathology specimen (e.g., histology specimen), the related case and patient information (e.g., specimen type, case and patient ID, parts within case, gross description, etc.) and information from the clinical system (e.g., assigned pathologist, specimens available for tests, etc.) into a digital storage device (e.g., hard drive, network drive, cloud storage, RAM, etc.)

In step 423, the method may include generating, for the one or more digital images, at least one of a prediction, a recommendation, and/or a plurality of data.

In step 425, the method may include generating a notification indicating that the at least one of the prediction, the recommendation, and/or the plurality of data is available. Additionally, a visualization for either an immunohistochemistry or genomic panel may be available.

In step 427, the method may include providing an option for a user to select a visualization and/or a report to review. The user may be a pathologist.

In step 429, the method may include generating a visualization of a recommended treatment pathway based on the at least one of the prediction, the recommendation, and/or the plurality of data. The treatment pathway (e.g., validated, new, clinical, etc.) or next steps (e.g., clinical trials, specialized doctor visit, etc.) may be based on the output/generated predictions. Visualizations of digital tumor profiler results can include one or more of a/an:
  a. Overlay (e.g., outline, gradient with color mapping to algorithmic predictions, etc.) on positive regions of interests on the original image. The overlay may be registered onto the subsequent image to guide the user to scrape a tumor for sequencing.
  b. Side-by-side comparisons of an image with prediction display and an image without prediction display
  c. Prioritized list (e.g., tumors with highest mutational burden, etc.) of top regions. The prioritized list may include a report that summarizes all parts analyzed for tumor-specific features (e.g., tumor mutational burden) with predictions In step 431, the method may include logging the visualization as a part of a case history within a clinical reporting system.

In step 433, the method may include integrating one or more test result within a final diagnostic report associated with the tissue specimen.

Figure 5:
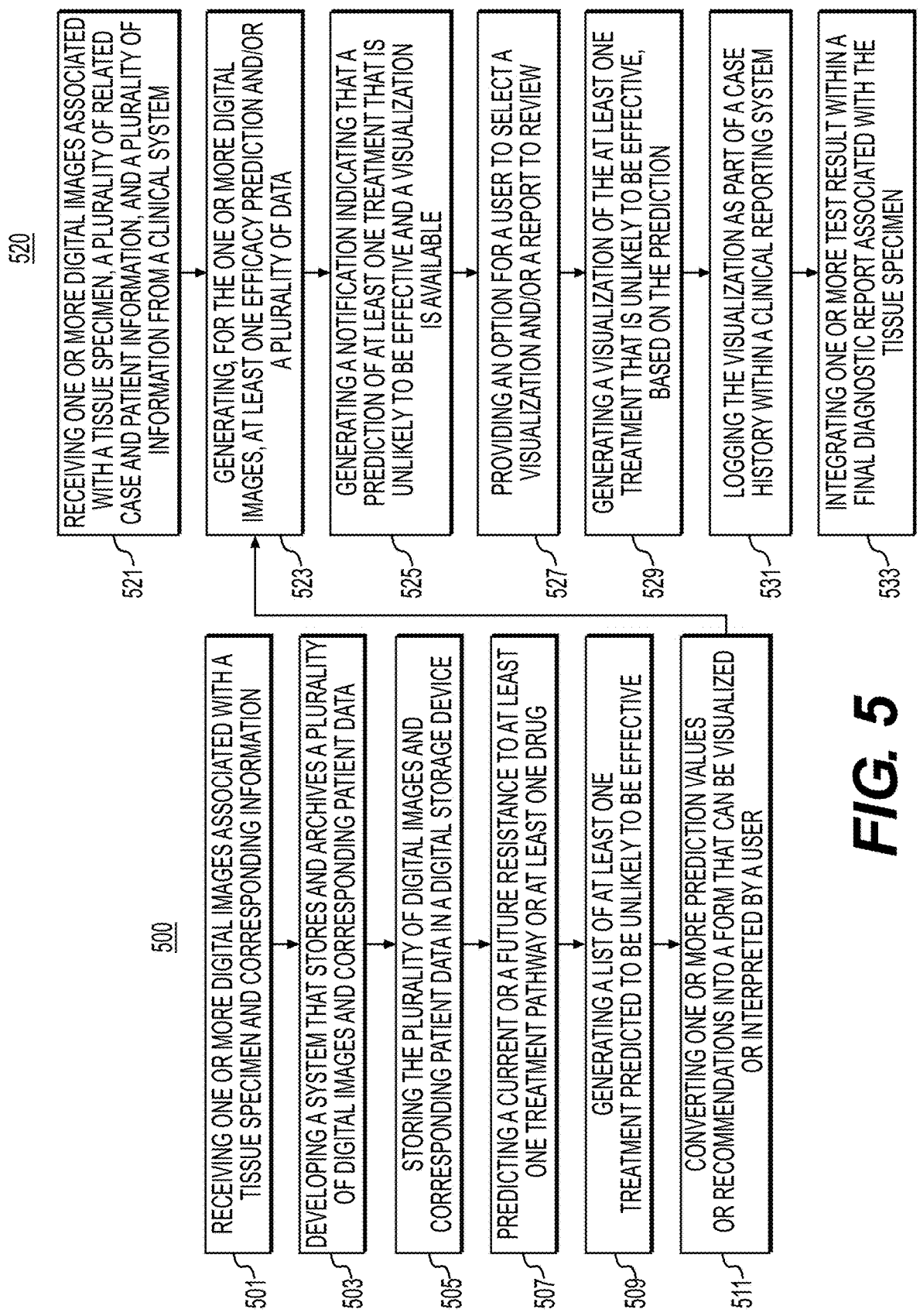
FIG. 5 is a flowchart illustrating an exemplary method for reporting predicted development of antineoplastic resistance, according to one or more exemplary embodiments of the present disclosure.

FIG. 5 is a flowchart illustrating an exemplary method for using and training a machine learning system to report on predicted development of antineoplastic resistance, according to one or more exemplary embodiments of the present disclosure. Antineoplastic resistance occurs when cancer cells resist and survive despite anti-cancer treatments. This ability can evolve in cancers during the course of treatment. Predicting which therapies the cancer will have the most difficulty acquiring resistance to may improve patient treatment and survival. Some cancers can evolve resistance to multiple drugs over the course of treatment. This may be delivered in order to identify treatments that are likely to be ineffective. An exemplary embodiment may be used to report on predicted development of antineoplastic resistance. The exemplary methods 500 and 520 may be used to predict development of antineoplastic resistance. Exemplary methods 500 and 520 (i.e., steps 501-511 and steps 521-533) may be performed by slide analysis tool 101 automatically or in response to a request from a user.

According to one embodiment, the exemplary method 500 for training a machine learning system to visualize tumor region to guide a molecular pathologist may include one or more of the following steps. In step 501, the method may include receiving one or more digital images associated with a tissue specimen and corresponding information. The one or more digital images may comprise histology slides. The corresponding information may comprise related information (e.g., specimen type, available parts, gross description, etc.), clinical information (e.g., diagnosis, biomarker information, etc.), and patient information (e.g., demographics, gender, etc.).

In step 503, the method may include developing a system that stores and archives a plurality of digital images and corresponding patient data. The corresponding patient data may comprise images from screening, follow-up, outcome, etc.

In step 505, the method may include storing the plurality of digital images and corresponding patient data in a digital storage device. The digital storage device may comprise a hard drive, a network drive, a cloud storage, a RAM, etc.

In step 507, the method may include predicting a current or a future resistance to at least one treatment pathway or at least one drug. The prediction may be using AI, testing, etc. The AI may infer this information using a variety of inputs including demographic information, digital images of the (stained) tissue containing a tumor, patient history, etc.

In step 509, the method may include generating a list of at least one treatment predicted to be unlikely to be effective.

In step 511, the method may include generating a list of at least one recommended treatment pathway based on a predicted tumor region. The recommended treatment pathway (e.g., drugs, clinical trials, etc.) and any related information (e.g., success rates, locations for treatment, etc.) may be based on the predicted tumor region.

In step 511, the method may include converting one or more prediction values or recommendations into a form that can be visualized or interpreted by a user (e.g., pathologist, patient, oncologist, etc.).

In step 521, the method may include receiving one or more digital images associated with a tissue specimen, a plurality of related case and patient information from a clinical system. The pathology specimen (e.g., histology specimen), the related case and patient information (e.g., specimen type, case and patient ID, parts within case, gross description, etc.) and information from the clinical system (e.g., assigned pathologist, specimens available for tests, etc.) into a digital storage device (e.g., hard drive, network drive, cloud storage, RAM, etc.)

In step 523, the method may include generating, for the one or more digital images, at least one efficacy prediction and/or a plurality of data.

In step 525, the method may include generating a notification indicating that a prediction of at least one treatment that is unlikely to be effective and a visualization is available.

In step 527, the method may include providing an option for a user to select a visualization and/or a report to review. The user may be a pathologist.

In step 529, the method may include generating a visualization of the at least one treatment that is unlikely to be effective, based on the prediction. Visualizations of information may be provided via a/an:

a. Interactive web interface, where a user (e.g., a pathologist, oncologist, patient, etc.) may learn more about at least one specific recommendation (e.g., open clinical trials, hospitals/physicians that specialize in the treatment, etc.) via the interface's direct links and sources (e.g., websites, literature, etc.).

b. Report, where the user may view a summarized, immutable report that may include, but is not limited to the following elements:
  i. Patient history
  ii. Case summary
  iii. Diagnostic summary
  iv. Digital and/or 'manual' test results
  v. Suggested next steps for the patient based on digital test results In step 531, the method may include logging the visualization as a part of a case history within a clinical reporting system.

In step 533, the method may include integrating one or more test result within a final diagnostic report associated with the tissue specimen.

FIG. 6 depicts exemplary options for a user to review a visualization and/or report, according to one or more exemplary embodiments of the present disclosure. In a display 60, an example report with a display of slide scoring results is shown. A display 65 shows an exemplary window with an option for a user to order a digital IHC run on a slide.

Figure 7:
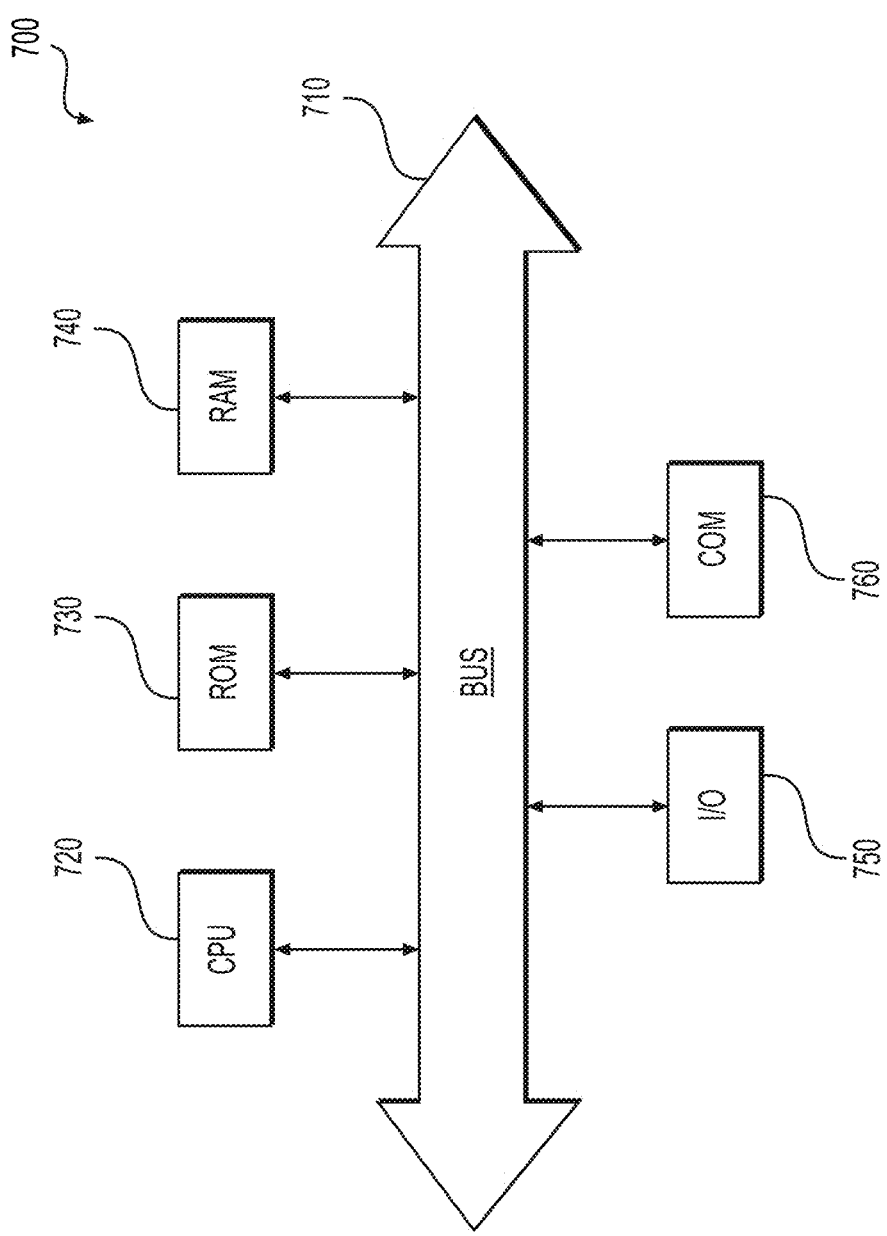
FIG. 7 depicts an exemplary system that may execute techniques presented herein.

As shown in FIG. 7, device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multi-processor system, such system operating alone, or in a cluster of computing devices operating in a cluster or server farm. CPU 720 may be connected to a data communication infrastructure 710, for example a BUS, message queue, network, or multi-core message-passing scheme.

Device 700 may also include a main memory 740, for example, random access memory (RAM), and also may include a secondary memory 730. Secondary memory 730, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include similar means for allowing computer programs or other instructions to be loaded into device 700. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 700 may also include input and output ports 750 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples to be considered as exemplary only.

What is claimed is:

1. A computer-implemented method for processing an electronic image corresponding to a specimen, the method comprising:
    receiving one or more digital images associated with a tissue specimen, a related case, a patient, and/or a plurality of clinical information;
    determining a prediction of a biomarker and a plurality of genomic panel elements, for the one or more digital images using a machine learning system, the machine learning system having been trained using a plurality of training images, to predict the biomarker and the plurality of genomic panel elements;
    generating, based on the prediction of the predicted biomarker and genomic panel elements, a list of recommended treatment pathways;
    determining, based on the prediction of the predicted biomarker and genomic panel elements, whether to log an output and at least one visualization region as part of a case history within a clinical reporting system; and
    generating one or more displays of at least one recommended treatment of the list of recommended treatment pathways based on the prediction of the predicted biomarker and genomic panel elements, through at least one of an overlay of at least one region of interest layered on top of the one or more digital images and a side by side visualization of the one or more digital images with the prediction displayed and the one or more digital images without the prediction displayed.

2. The computer-implemented method of claim 1, wherein the method further comprises generating a notification indicating that the prediction or the side by side visualization for the one or more digital images is available.

3. The computer-implemented method of claim 1, wherein the method further comprises generating an option for a user to review the prediction or the side by side visualization.

4. The computer-implemented method of claim 1, wherein the side by side visualization comprises digital immunohistochemistry or genomic panel results comprising a summary of digital tests run with at least one result.

5. The computer-implemented method of claim 1, wherein determining the prediction comprises:
    receiving one or more digitized images of a pathology specimen, related information, clinical information, and patient information;
    developing a system that stores and archives a plurality of images and a plurality of corresponding patient data;
    determining at least one predicted biomarker and at least one predicted genomic panel element, based on the plurality of images and the plurality of corresponding patient data; and
    converting one or more prediction value and at least one treatment pathway recommendation to a form readable by a user.

6. The computer-implemented method of claim 5, further comprising outputting the one or more prediction value and the at least one treatment pathway recommendation to a user interface.

7. The computer-implemented method of claim 5, wherein the at least one treatment pathway is based on a plurality of clinical practice guidelines.

8. The computer-implemented method of claim 1, wherein the at least one treatment pathway comprises a validated treatment pathway, a new treatment pathway, and/or a clinical treatment pathway based on the prediction.

9. A system for processing an electronic image corresponding to a specimen, the system comprising:
    at least one memory storing instructions; and
    at least one processor configured to execute the instructions to perform operations comprising:
        receiving one or more digital images associated with a tissue specimen, a related case, a patient, and/or a plurality of clinical information;
        determining a prediction of a biomarker and a plurality of genomic panel elements, for the one or more digital images using a machine learning system, the machine learning system having been trained using a plurality of training images, to predict the biomarker and the plurality of genomic panel elements;
        generating, based on the prediction of the predicted biomarker and genomic panel elements, a list of recommended treatment pathways;
        determining, using the machine learning system and based on the prediction, whether to log an output and at least one visualization region as part of a case history within a clinical reporting system; and
        generating a visualization of digital immunohistochemistry or genomic panel results based on the prediction of the predicted biomarker and genomic panel elements by at least one of an overlay of at least one region of interest layered on top of the one or more digital images and a side by side visualization of the one or more digital images with the prediction displayed and the one or more digital images without the prediction displayed.

10. The system of claim 9, the operations further comprising:
generating a notification indicating that the prediction or the visualization for the one or more digital images is available.

11. The system of claim 9, the operations further comprising: generating an option for a user to review the prediction or the side by side visualization.

12. The system of claim 9, the operations further comprising: generating one or more displays of at least one recommended treatment based on the prediction.

13. The system of claim 9, the operations further comprising:
generating one or more displays of at least one recommended treatment based on the prediction, through at least one of through at least one of an overlay of at least one region of interest layered on top of the one or more digital images and a side by side visualization of the one or more digital images with the prediction displayed and the one or more digital images without the prediction displayed.

14. The system of claim 9, wherein the recommendation of at least one treatment pathway is based on a plurality of clinical practice guidelines.

15. The system of claim 9, wherein determining the prediction comprises:
receiving one or more digitized images of a pathology specimen, related information, clinical information, and patient information;
developing a system that stores and archives a plurality of images and a plurality of corresponding patient data;
determining at least one predicted biomarker and at least one predicted genomic panel element, based on the plurality of images and the plurality of corresponding patient data; and
converting one or more prediction value and at least one treatment pathway recommendation to a form readable by a user.

16. The system of claim 15, the operations further comprising outputting the one or more prediction value and the at least one treatment pathway recommendation to a user interface.

17. The system of claim 9, wherein the at least one treatment pathway comprises a clinical trial and/or a treatment based on the prediction.

18. A non-transitory computer readable medium storing instructions that, when executed by a processor, cause the processor to perform operations for monitoring health of a population, the operations comprising:
receiving one or more digital images associated with a tissue specimen, a related case, a patient, and/or a plurality of clinical information;
determining a prediction of a biomarker and a plurality of genomic panel elements, the one or more digital images using a machine learning system, the machine learning system having been trained using a plurality of training images, to predict the biomarker and the plurality of genomic panel elements;
generating a list of recommended treatment pathways based on the prediction of the predicted biomarker and genomic panel elements;
determining, based on the prediction of the predicted biomarker and genomic panel elements, to log an output and at least one visualization region as part of a case history within a clinical reporting system; and
generating one or more displays of at least one recommended treatment, based on the prediction of the predicted biomarker and genomic panel elements, through at least one of an overlay of at least one region of interest layered on top of the one or more digital images and a side by side visualization of the one or more digital images with the prediction displayed and the one or more digital images without the prediction displayed.

19. The computer readable medium of claim 18, wherein the operations further comprise generating a notification indicating that the prediction or the side by side visualization for the one or more digital images is available.

* * * * *